US008771938B2

(12) United States Patent
Chang et al.

(10) Patent No.: US 8,771,938 B2
(45) Date of Patent: Jul. 8, 2014

(54) MICROFLUIDIC PLATFORMS FOR MULTI-TARGET DETECTION

(75) Inventors: Hsueh-Chia Chang, Granger, IN (US); Jason Gordon, Kansas City, MO (US); Satyajyoti Senpati, South Bend, IN (US); Zachary Gagnon, Mishawaka, IN (US); Sagnik Basuray, Mishawaka, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 532 days.

(21) Appl. No.: 12/246,987

(22) Filed: Oct. 7, 2008

(65) Prior Publication Data

US 2009/0092989 A1    Apr. 9, 2009

Related U.S. Application Data

(60) Provisional application No. 60/978,544, filed on Oct. 9, 2007, provisional application No. 61/127,812, filed on May 15, 2008.

(51) Int. Cl.
| | | |
|---|---|---|
| C12Q 1/68 | (2006.01) | |
| C12P 19/34 | (2006.01) | |
| C12M 1/36 | (2006.01) | |
| C12M 1/34 | (2006.01) | |
| G01N 15/06 | (2006.01) | |
| G01N 27/00 | (2006.01) | |
| B01J 19/08 | (2006.01) | |
| B01D 57/02 | (2006.01) | |
| B03C 5/02 | (2006.01) | |
| C02F 1/48 | (2006.01) | |
| C07H 21/02 | (2006.01) | |
| C07H 21/04 | (2006.01) | |

(52) U.S. Cl.
USPC ....... 435/6.1; 435/91.1; 435/91.2; 435/286.5; 435/286.7; 435/287.2; 422/68.1; 422/82.01; 422/186.26; 204/450; 204/547; 204/600; 204/643; 536/23.1; 536/24.3; 977/702; 977/742; 977/773

(58) Field of Classification Search
USPC .............. 435/6.1, 91.1, 91.2, 286.5, 286.7, 435/287.2; 204/450, 547, 600, 643; 422/68.1, 82.01, 186–26; 536/23.1, 536/24.3; 977/702, 742, 773
See application file for complete search history.

(56) References Cited

U.S. PATENT DOCUMENTS

| | | | | |
|---|---|---|---|---|
| 5,387,510 | A   * | 2/1995  | Wu             | 435/91.2 |
| 6,168,948 | B1 * | 1/2001  | Anderson et al. | 435/287.2 |
| 6,663,615 | B1 * | 12/2003 | Madou et al.   | 604/891.1 |
| 7,081,192 | B1 * | 7/2006  | Wang et al.    | 204/547 |
| 7,327,459 | B2   | 2/2008  | Kim et al.     | |
| 2004/0011650 | A1 * | 1/2004 | Zenhausern et al. | 204/547 |
| 2005/0026202 | A1   | 2/2005 | Edman et al.   | |
| 2005/0048519 | A1 * | 3/2005 | Chien et al.   | 435/6 |
| 2006/0068378 | A1   | 3/2006 | Mirkin et al.  | |
| 2006/0102482 | A1 * | 5/2006 | Auerswald et al. | 204/547 |
| 2006/0177815 | A1 * | 8/2006 | Soh et al.     | 435/4 |
| 2006/0201811 | A1 * | 9/2006 | Hamers et al.  | 204/547 |

OTHER PUBLICATIONS

Muthiah et al, A simple multiplex PCR method for the concurrent detection of three CYP2C* variants, 2004, Clinica Chemica Acta, 349, 191-198.*
Makowski et al, Enhanced direct amplification of Guthrie card DNA following selective elution of PCR inhibitors, 1995, Nucleic Acids Research, 23, 3788-3789.*
Graham et al, Simple multiplex genotyping by surface enhanced resonance raman scattering, 2002, Anal. Chem., 74, 1069-1074.*
Gurtner et al, Microelectronic aray devices and techniques for electric field enhanced DNA hybridization in a low conductance buffers, 2002, Electrophoresis, 23, 1543-1550.*
Zhou et al, Bacteria capture, concentration and detection by alternating current dielectrophoresis and self assembly of dispersed single wall carbon nanotubes, 2006, Electrophoresis, 27, 1376-1385.*
Streptavidin coated beads brochure from Bang laboratories, Fishers Indiana, pp. 1-4, printed on Apr. 21, 2011.*
"PCT International Search Report," issued by the International Searching Authority on Mar. 17, 2009, in connection with international application No. PCT/US08/79094 (2 Pages).
"PCT Written Opinion," issued by the International Searching Authority on Mar. 17, 2009, in connection with international application No. PCT/US08/79094 (9 Pages).
Written Opinion of the International Searching Authority.
The Patent Office of the People's Republic of China, First Office Action issued on Chinese Patent Application No. 200880119892.X which is a counterpart of U.S. Appl. No. 12/246,987, issuing date Jul. 24, 2012, 4 pgs.

* cited by examiner

*Primary Examiner* — Narayan Bhat
(74) *Attorney, Agent, or Firm* — Greenberg Traurig, LLP

(57) ABSTRACT

Disclosed are example methods and devices for detecting one or more targets. An example method includes placing a sample including a first target with in a microfluidic device and hybridizing a plurality of copies of the first target with a plurality of nanostructures. The example method includes applying an electric current to the plurality of nanostructures and using an electric field created by the electric current to move the plurality of nanostructures. In addition, the plurality of nanostructures are sorted and evaluated to determine at least one of a presence, an absence, or a quantity of the first target.

25 Claims, 14 Drawing Sheets

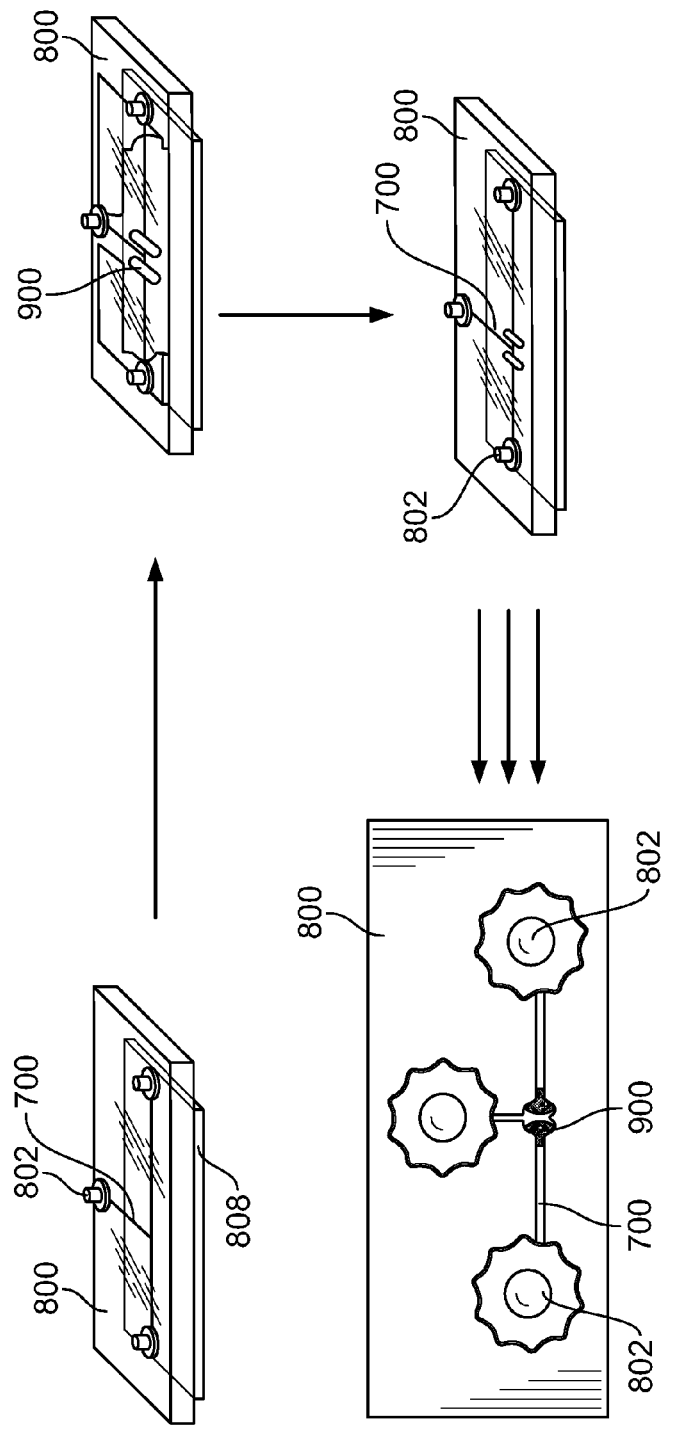
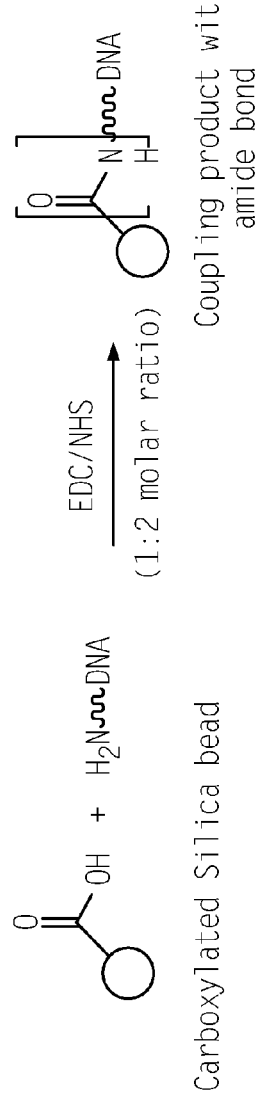
FIG. 9
FIG. 10

MICROFLUIDIC PLATFORMS FOR MULTI-TARGET DETECTION

RELATED APPLICATION

This application claims priority to U.S. Provisional Patent Application No. 60/978,544, entitled "Nano-Bead Electrokinetics: Enabling Microfluidic Platform for Rapid Multi-Target Detection," filed on Oct. 9, 2007, and to U.S. Provisional Patent Application No. 61/127,812, entitled, "Rapid, Mismatch-Free and Strong Hybridization Technique for High-Throughput Genetic Surface Assays," filed on May 15, 2008, both of which are hereby incorporated by reference in their entireties.

FIELD OF THE DISCLOSURE

This disclosure relates generally to microfluidic devices, and, more particularly, to microfluidic platforms for multi-target detections.

BACKGROUND

Diagnostic assays are biochemical techniques that may be used to detect and identify pathogens (e.g., harmful bacteria, viruses, organism, etc.) and/or diseased cells. One known diagnostic assay involves the use of polymerase chain reaction (PCR), which uses a DNA polymerase to amplify a piece of DNA, i.e., a target DNA, by in vitro enzymatic replication. PCR is capable of rapidly amplifying a DNA sequence initially present in minute concentrations, ultimately producing millions of identical DNA molecules and, thus, exponentially increasing the detection sensitivity toward the respective DNA sequence/target.

Some diagnostic assays also include selectively capturing detection targets such as amplified DNA sequences, biomarker molecules, pathogens and/or other targets, removing the targets from a large sample and docking the targets to a molecular probe. The docked targets can be detected with various techniques including optical sensor technologies that are based on fluorescent tagging or emission, Raman, and IR or UV spectroscopy.

These diagnostic assays are routinely used in genetic diagnostic techniques in medical diagnostic laboratories. In addition, grocery stores, food growers, processors, distributors and/or manufacturers use diagnostic assays such as enzyme-linked immunosorbent assays to detect bacteria such as E. Coli in fresh produce. While these techniques are useful for bacteria detection or the detection of other DNA, biomarkers or other targets, they are typically encumbered by expensive, slow, and heavy laboratory equipment, often require extensive manual supervision and handling, and take days or longer to produce results (e.g., TB bacteria require a week to culture).

Portable PCR kits are also commercially available; however, these assays have at least an hour-long response time, which is typically too long for portable field-use devices or for high-throughput biomarker screening. In addition, the conventional assays kits still perform single-target detection using a batch format with low-throughput, which has a low target count and questionable sensitivity.

BRIEF DESCRIPTION OF THE DRAWINGS

FIG. 9 shows an example fabrication of example filters on the example glass slide of FIG. 8.

FIG. 10 illustrates an example functionalization of an example oligomer probe on an example nanostructure.

DETAILED DESCRIPTION

Figure 1:
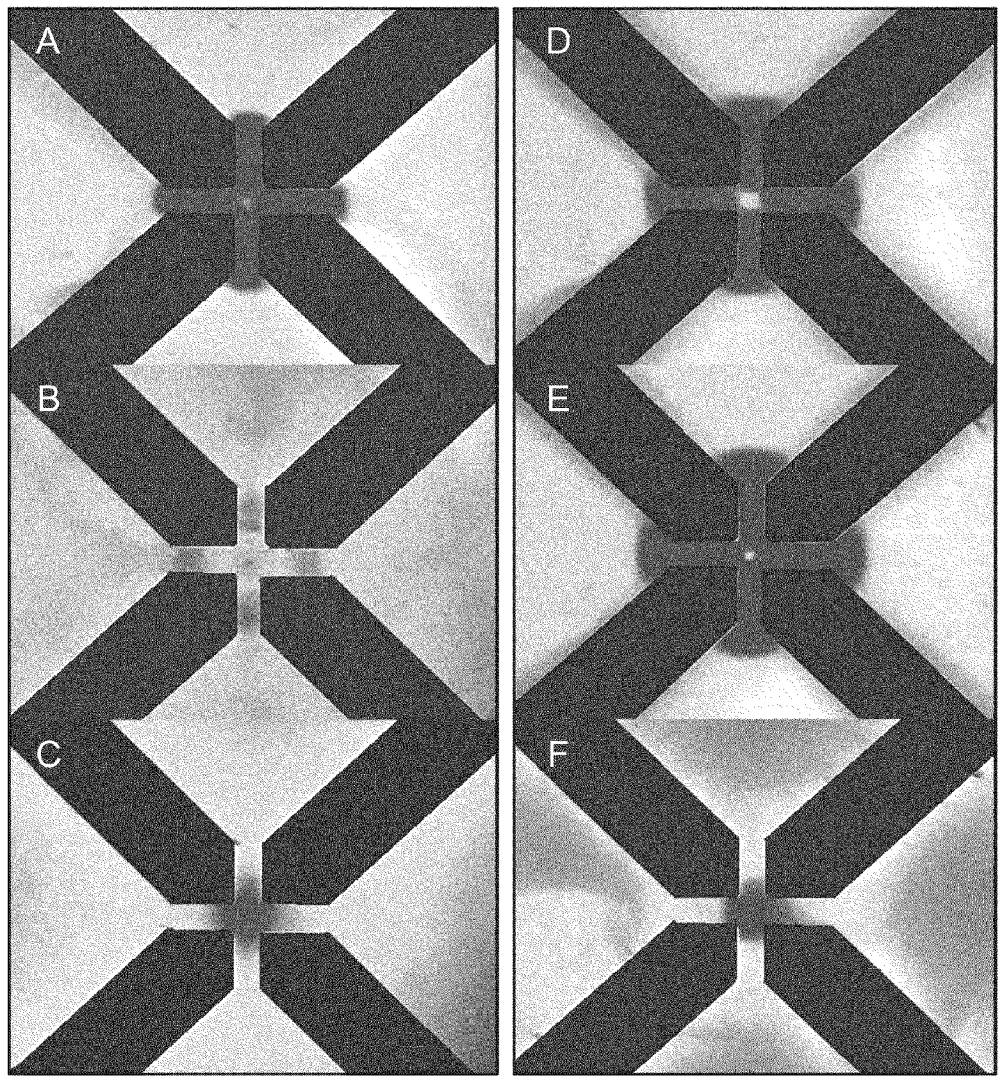
FIGS. 1A-1F are images of example patterns formed by example docked and undocked nanostructures in the vicinity of a quadrupole electrode.

The example devices and methods described are directed to detecting one or more targets such as, for example, a pathogen and/or diseased cell. An example method includes placing a sample including a first target within a microfluidic device and hybridizing a plurality of copies of the first target with a plurality of nanostructures. The example method includes applying an alternating-current electric current to the plurality of nanostructures and using an electric field created by the electric current to trap and move the nanostructures. The trapping allows a rapid flow of samples across the nanostructure, thus allowing the capture of targets from more than, for example, 100 microliters of sample solution. The nanostructures are then sorted and evaluated to determine the presence or absence of the first target, which may include, for example, determining the quantity of the target.

Furthermore, the sample flow is driven by an externally or internally applied pressure supplied by, for example, a mechanical syringe pump, a manually driven syringe pump, micro-pumps, and/or other suitable devices. Pressure-driven continuous flow allows the sampling of a large-volume sample and prevents clogging of the channels and orifices by debris, and is hence desirable for a high-throughput portable device. Thus, the sorting and trapping and other aspects of the example method and system described herein work under pressure and, thus, are resistant to blockages, debris and/or other obstructions. In other words, the presence of increased pressure does not impede operation of the example method or systems described herein.

An example device that serves as a target detector unit includes an inlet of a microfluidic device into which a sample of a first target is placed and a hybridization chamber to dock a plurality of copies of the first target with a plurality of nanostructures. In addition, the example device includes a focuser to focus the nanostructures, a sorter to sort the nanostructures, and a trap to collect the sorted nanostructures.

Another example method to detect a target includes obtaining a sample including the target and replicating the target in the sample to produce an amplified mixture. This example method includes coupling a nanostructure to a chamber and functionalizing a molecular probe to the nanostructure. The example method includes flowing the amplified mixture through the nanostructure to hybridize the target in the amplified mixture. The hybridization yield and rate are both enhanced by the presence of an alternating or direct current electric field. Also, the presence or absence of the target is detected by any suitable detection device and/or methods.

Another example target detector includes a replication chamber in which a target is replicated to produce an amplified mixture and a microfluidic chamber containing nanostructures having molecular probes functionalized thereto. The example target detector also includes a filter to hold nanostructures in the microfluidic chamber, a channel by which the amplified mixture flows through the nanostructure to hybridize the target in the amplified mixture, and a detector to determine the presence or absence of the target.

Yet another example method for detecting a plurality of targets includes inserting a sample including one or more targets into a microfluidic device, holding the targets in a reservoir, passing the targets through to a plurality of detection tubes, and hybridizing the targets. The example method also includes detecting the presence or absence of the targets by any suitable detection device and/or methods.

Still another example target detector for detector multiple targets includes an injection pore for accepting a sample including one or more targets into a microfluidic device, a reservoir for holding the targets, a plurality of detection tubes communicatively coupled to the reservoir, and a hybridization chamber in the plurality of detection tubes. The additional alternative example target detection device similarly includes a detector to detect the presence or absence of the targets.

Operation of the example devices and methods described herein include obtaining samples from a patient and/or the environment for testing for, for example, defense, homeland or national security, medical, research, environmental, process control applications or any other suitable purpose. Some samples may require pretreatment before further tests are completed. Pretreatment may include, for example, filtering, precipitation with chemical reagents and/or breakdown of physical debris and/or chemical inhibitors for the removal of the debris and/or the inhibitors, physically, chemically or otherwise, from the sample. Pretreatment may also include, in some example, a number of other various procedures.

Molecular detection targets are added to the sample. Molecular detection targets may include, for example, biomarkers or genes. Some example biomarkers include biological vesicles, peptides and/or other non-DNA molecules. Genes include strands of DNA and/or RNA. In some examples, if the target includes genes, PCR may be used to replicate/amplify the number of DNA and/or RNA strands in the sample.

The detection targets are hybridized (i.e., docked) with complementary molecular probes that are functionalized (i.e., chemically attached) onto nanostructures. Hybridization of targets on nanostructures can be facilitated by the presence of an electric field such as, for example, a field produced by an AC current. The presence of the electric field greatly reduces the amount of time needed for hybridization. In some examples, hybridization may occur in less than about one second as the detection targets are introduced to the nanostructures. Reduced hybridization time is beneficial for a high throughput portable device. Example nanostructures include carbon nanotubes (CNT), nanobeads, nanowires, nanocolloids, nanoparticles, nanorods, quantum dots, nanocrystals, liposomes, silica beads, latex beads, gold colloids and/or other structures of any other geometry with dimensions on the sub-micron scale, i.e., less than one micron. The molecular probes with which the nanostructures may be functionalized may include, for example, oligomers, probes, fluorophores, carboxyl groups, streptavidin/avidin or other suitable molecular probe(s) to render the microstructures hydrophilic. There are various advantages to utilizing each of the different nanostructures as a molecular probe. For example, latex particles with uniform size are easily synthesized, while the functionalization of silica nanobeads with different chemical and molecular probes has been routinized. Probe and fluorophore attachment to CNT is also relatively simple. Nanowires allow easier coding (e.g., the addition of fluorescent dyes and/or other signatures on different nanowires), and CNTs offer better specificity as molecules do not adsorb indiscriminately on CNTs due to electrostatic interaction. The conductance of the CNT is also sensitive to molecular hybridization such that target hybridization event produces a large electric impedance signal. Furthermore, different fluorescent dyes can be attached sequentially on a colloid, a liposome, or a nanowire to provide a fluorescent bar code or other signature, as noted herein.

As described in greater detail below, there are varying manners in which the detection target may be hybridized. For example, genes may be hybridized with complementary molecular probes (e.g., oligo-nucleotides, which are also DNA) via hydrogen bonding. If biomarkers are used as the detection target, the biomarkers dock with the nanostructure. Thus, hybridization is between a molecule of the biomarker and a complementary molecule on the nanostructure. In the example in which the biomarker is a molecule, hybridization would occur between the biomarker itself and a complementary molecule on the nanostructure. Such hybridization involves hydrogen bonding, or any other suitable chemical and/or physical bonding mechanisms. Another example hybridization involves biotin-streptavidin, as detailed below.

The detection targets may be detected in various ways. For example, in some examples, dielectrophoresis (DEP) is applied to the docked nanostructures to subject the nanostructures to an electric field to move the nanostructures into various patterns and/or to measure the impedance of the solution containing the nanostructures. In other examples, detection occurs through optical observation of, for example, fluorescent properties (e.g., intensity) of the solution containing the nanostructures. In another example, measurement and/or observation of both fluorescence and impedance may be employed One example diagnostic kit or detection device that may be used to detect targets includes an integrated, continuous-flow dielectrophoretic platform. A micro/nanostructure platform based on DEP, which includes the use of an AC electric field to impart a particle force, manipulates a nanostructure such that the microfluidic platform detects and identifies the target. Specifically, DEP refers to the migration of a particle (which need not be charged) under the influence of an electric field gradient. The electric field induces a particle dipole on each individual nanostructure when exposed to a non-uniform field. The nanostructures experience a net force causing controlled migration, described as either positive DEP (p-DEP) or negative DEP (n-DEP) depending on whether the migration is toward or away from a high-field region. As the applied frequency is increased, most nanostructures will switch from p-DEP to n-DEP. The point at which a nanostructure switches is the "cross-over" point. Exploiting differences in the "cross-over" frequency between nanostructures provides a way to rapidly impart different particle forces on distinct nanostructure(s) such as forces in different directions.

The DEP direction of nanostructures can be reversed by molecular docking. For example, docking changes the surface conductance and the effective size of the functionalized nanostructures, which can change the induced dipole moment of the nanostructure in a non-uniform AC electronic field. As a consequence, the nanostructures assemble into distinctly different patterns in a non-uniform AC electric field depending on whether docking/hybridization has occurred.

For example, FIGS. 1A-F show nanostructure suspensions in the vicinity of a quadrupole electrode. The nanostructure suspensions are undocked in FIGS. 1A-C and docked in FIGS. D-F. In addition, FIGS. 1A and 1D show the nanostructure suspensions at a frequency of 300 KHz, FIGS. 1B and 1E show the nanostructure suspensions at a frequency of 700 KHz, and FIGS. 1C and 1F show the nanostructure suspensions at a frequency of 2.1 MHz. As shown in FIGS. 1A-F, nanostructure suspensions with and without DNA-oligomer hybridization (i.e., docked and undocked) exhibit distinctly different patterns at different AC frequencies. The patterns can be used to identify hybridization rapidly without labeling or tagging reagents. The detection can be done with a portable optical microscope instead of a confocal fluorescent microscope. The more evident the hybridization (i.e., the binding of detection targets to the nanostructures) and the greater the hybridization, the greater the presence of the target in the original sample and, thus, in the patient or the environment, which may provide useful information for, for example, defense, homeland or national security, medical, research, environmental, process control applications or any other suitable purpose.

Because the nanostructures move under the electric fields, the difference in force direction may be used to separate and sort the nanostructures or, in some examples, as detailed below, hold the nanostructures in place. In addition, DEP sorting, unlike cytometry, does not require identification of the nanostructures prior to sorting. This technique can be applied to DNA-oligomer hybridization, protein-DNA, antibody-antigen (e.g., biotin-streptavidin, as discussed below), and other molecular docking assays involving surface functionalized nanostructures, without requiring labeling or other reagents.

In addition, binary, ternary, or quaternary suspensions of nanostructures can provide an even richer spectrum of patterns that can be used for multi-target detection. Suspensions with, for example, nanostructures of different geometries and size, can also contribute to the complexity. Lastly, with biometrics integration, a large library of patterns could be produced. Access to a library of patterns will facilitate target detection by comparing observed patterns with known patters to determine the presence or absence of one or more target(s) as detailed herein.

The example DEP platforms described herein, like the electrokinetic flow-control components, are extremely portable because only microbatteries and microtransformers are required. As the on-chip optical sensors are controlled electronically, a fully integrated electronic supervising structure for the entire device/chip can then be implemented with a minimum of actuators and sensors. In addition, mechanical moving parts are kept to a minimum. For instance, in some examples, the only mechanical moving parts are a few ball valves. Reduction of the number of mechanical moving parts reduces chip fabrication costs. Furthermore, feedback control and automation may be implemented with a supervising microcircuit structure.

Figure 2:
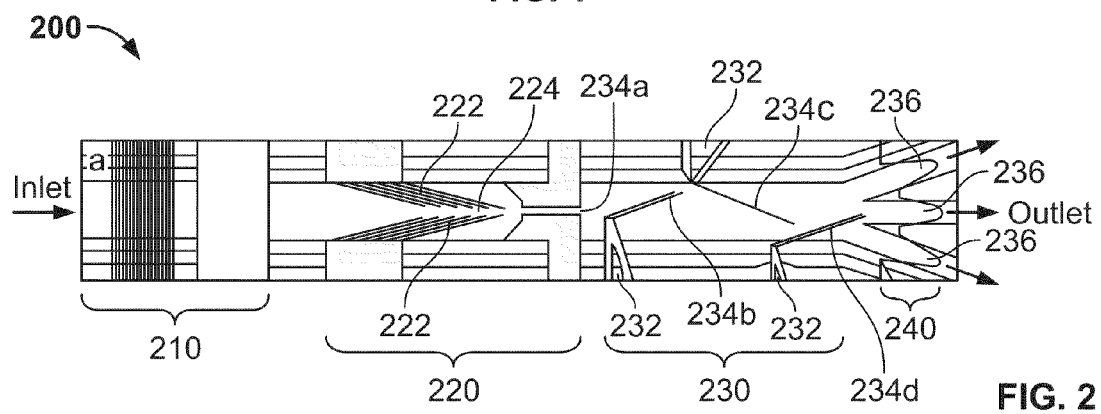
FIG. 2 is a schematic diagram of an example integrated multiplex continuous-flow dielectrophoresis sorting device.

FIG. 2 shows an example integrated multiplex continuous-flow DEP sorting device/chip 200 that allows sensor-free nanostructure sorting and identification. In this example, the chip 200 includes three different sequential DEP components and can sort three different nanostructures into three different channels at a speed of, for example, about 100 nanostructures per second. The chip 200 and any periphery equipment can be hand held, disposable, and fabricated at a low price such as, for example, less than about USD $1.00. The sorted nanostructures can be captured by a DEP trap within each channel without the use of a microfilter. The concentrated nanostructures can then be further probed with on-chip or off-chip sensors and detectors. The nanostructures also may be counted, for example, by measuring the impedance of one or more trapping electrodes.

In addition, one or more example chips 200 may be connected in series or in parallel and used in a modular fashion to achieve massively parallel screening. This modular form facilitates scaling up to accommodate sample probing with massively large numbers of different targets. Such a configuration may also allow side streams and recycle streams.

The different components of the example integrated DEP chip module 200 exploit the different particle forces experienced by the different nanostructures in different directions near the microelectrode components producing a high-electric field. As noted above, the example chip 200 includes consists of three stages downstream of a coarse DEP debris filter 210 (which, as noted above, may be used to pretreat a sample). The first stage 220 is a focusing unit that operates at the n-DEP region of all particles. The focusing stage 220 includes two side arrays of electrodes 222 with a decreasing gap width and at a frequency higher than the cross-over frequency of most nanostructures. The decreasing aperture of the gap 224 focuses substantially all nanostructures in the continuous stream into a region less than about, for example, 10 microns wide at the middle of the channel. The focused nanostructures form a linear, single-file queue, and can then be interrogated individually downstream. The second unit 230 includes three DEP sorters 232, each one consisting of an oblique electrode at the top substrate and a mirror image electrode (not shown) at the bottom. The gap between the electrode pairs sustains a high-field that would repel n-DEP nanostructures and allow p-DEP nanostructures to pass, thus, effecting separation of these nanostructures. The n-DEP nanostructures move along the oblique electrode pair, and are then released to the next sorter at a different streamline 234a-d from the p-DEP nanostructures. The nanostructures can, hence, occupy four possible streamlines 234a-d after the sorting unit 230: the original focused streamline plus the ones that pass through the tips of the three sorters 232. These streamlines 234a-d can then be fed into four different channels 236. Given the resolution of the focusing unit 220 shown in the example of FIG. 2, only three sorting channels 236 are used at high-throughput operating conditions. By using different frequencies at different gates, three different nanostructures can be sorted into three separate channels. In the final stage, a 3-D trap 240 is fabricated to capture all of the nanostructures in each of the channels, while the solution flows through the gap without extra hydrodynamic resistance.

Figure 3:
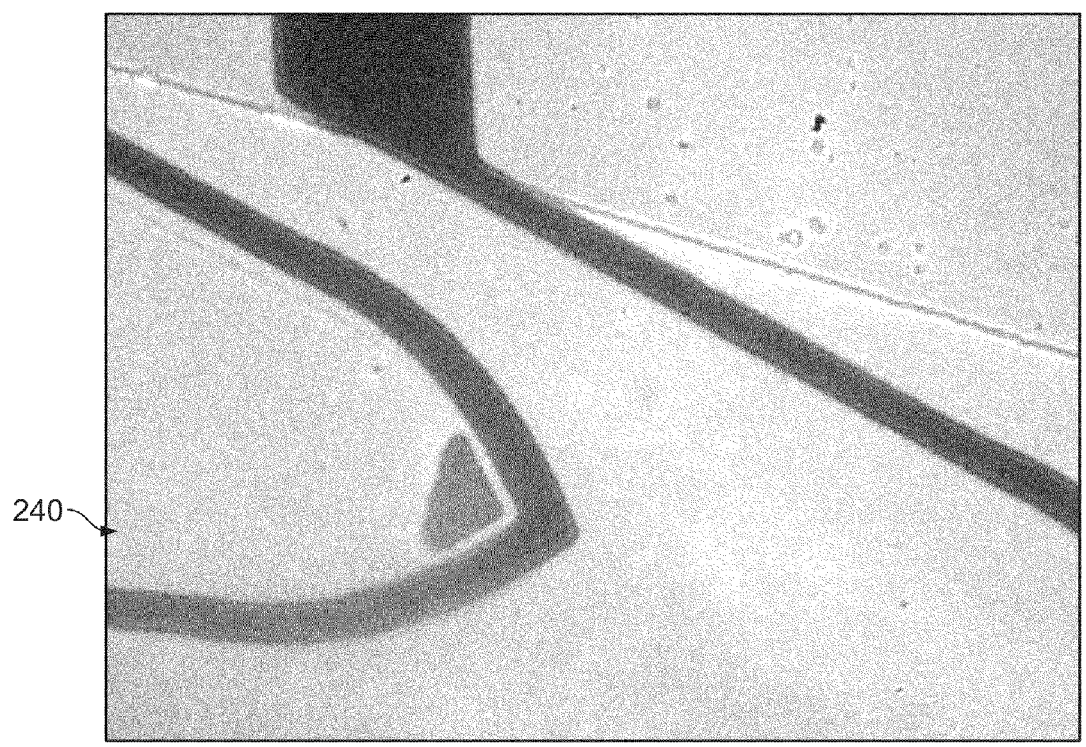
FIG. 3 is a photograph of a magnified example trapping of example docked nanostructures.

When massively parallelized or serialized, this continuous flow chip 200 allows high-throughput, label-free sorting without using molecular-sieves or microfilters that introduce significant hydrodynamic resistance. By using frequencies specific to certain nanostructures, the integrated sorters 232 and traps 240 offer much higher specificity than molecular nanosieves. Impedance measurement at the trap electrode can estimate the number of nanostructures trapped. An example trapping of a queue of nanostructures is seen in FIG. 3. In this example, nearly 80% separation efficiency can be achieved for binary separation at about 100 particles per second. Therefore, two or three modules in series can achieve approximately 99% purity.

Figure 4:
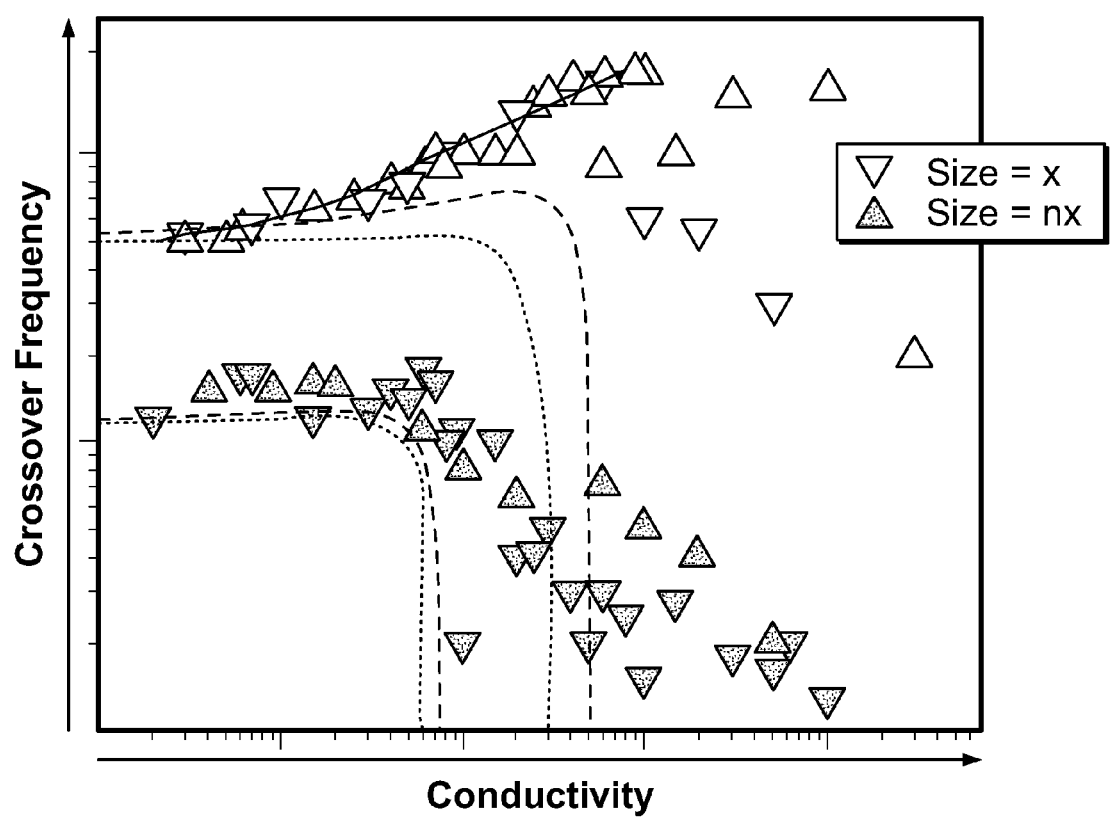
FIG. 4 is a graph plotting conductivity against crossover frequency for differently sized example docked nanostructures.

By sorting nanostructures with docked antigens (or hybridized genetic nanostructures) from the undocked ones, the above unit offers a simple means of continuous-flow, multi-target detection with different nanostructures and without (or in addition to) optical sensing or fluorescent labeling. The docked nanostructures have a distinctly different DEP mobility and/or cross-over frequency from the undocked ones. The DEP mobility is size-sensitive, and though smaller nanostructures may be more sensitive to molecular anchoring of the DNA targets, for example, the nanostructures cannot be too small or the mobilities will become insignificant. An optimum size may be between about 50 and 500 nm, which would allow, for example, DEP velocity as high as about 100 μm/s. Because the DEP mobility is size-sensitive, nanostructures with roughly the same dimension as the docked molecule should have different DEP mobilities before and after the molecular docking event. Also, DNAs are conducting molecules and their docking can significantly increase the particle conductivity of small nanostructures relative to that of the buffer solution. For example, FIG. 4 shows that as conductivity increases, the difference between crossover frequencies for differently sized nanostructures increases disproportionately. For example, two nanostructures having a size ratio of about six may have a cross-over frequency that is only about a factor of five different for conductivities lower than about 1 mS/m. At higher conductivities, the cross-over frequency between the two nanostructures may be different by about two-orders of magnitude.

Figure 5:
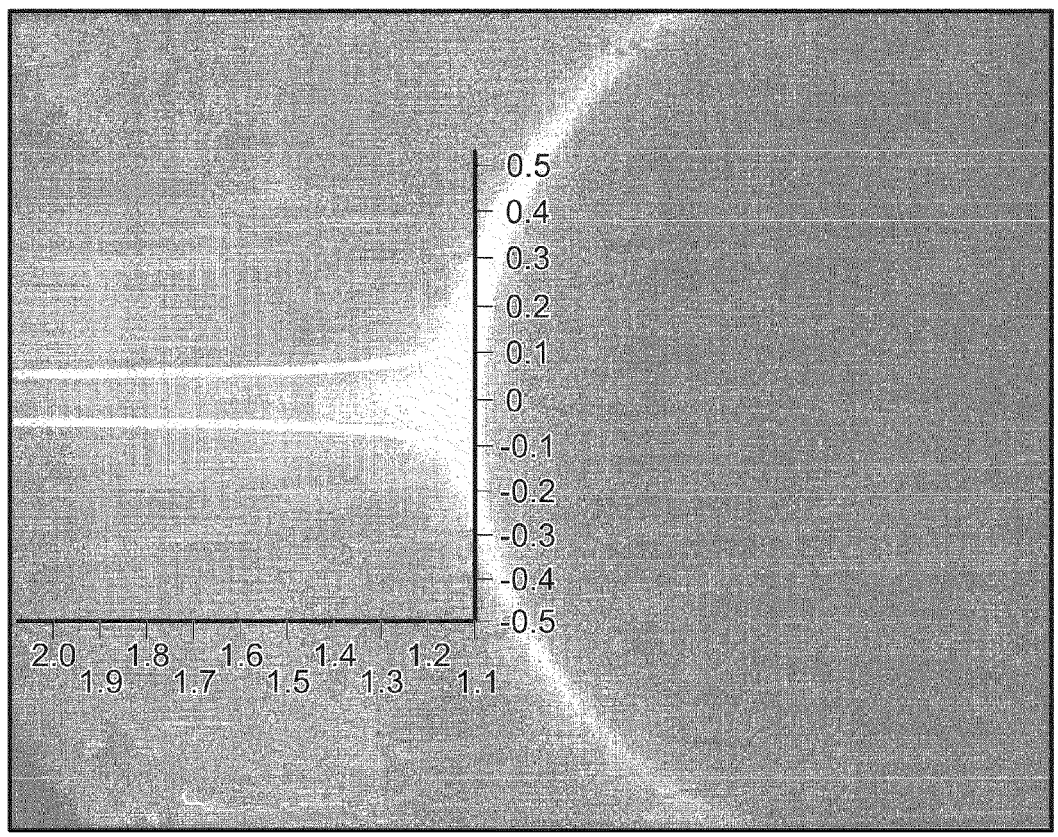
FIG. 5 is a magnified image of the conductive charging of the poles of an example docked nanostructure.

FIG. 5 shows an example conductive charging of the poles of a nanostructure. Charged fluorescent dye accumulates at opposite poles for each half cycle and increases its concentration (e.g., about six orders of magnitude), as evident by the much higher fluorescent intensity at the poles. The same normal charging of the double layer, tangential migration and pole concentration mechanism can concentrate negatively charged DNAs at one pole of the nanostructure. These docked DNA molecules, in turn, change subsequent conductive polarization at the poles and affect the cross-over frequency of the nanostructure. Thus, hybridized and unhybridized nanostructure suspension exhibit different patterns at the same frequency (see FIG. 1A-F). Thus, there is a difference in the cross-over frequency between docked and undocked nanostructures due to the double layer effects, and the DEP platform 200 can effectively sort these two nanostructures without the need for a sensor.

In addition, as detailed herein, the geometry and material of the nanostructure, the permittivity, conductivity and ion valency of the buffer and nanostructure-nanostructure interaction all affect the DEP behavior of the nanostructures and influence sorting. In the illustrated example, the length of the probe 232 affects the frequency at which cross-over occurs. Some nanostructures such as, for example, CNT and slender nanowires, have far higher DEP mobilities (due to field focusing by the slender geometry), more selective molecular capture, negligible dye adsorption, and therefore may be the preferable nanostructures for some example DEP platforms. In addition, CNT and slender nanowires also are relatively easy to barcode. In fact, CNTs dock with bacteria much more readily than nanospheres, and the docked CNTs can actually enhance the DEP of the aggregate and become DEP transporters of the target, e.g., a pathogen.

In addition, buffer tuning may need to be implemented in situations in which, for example, zwitterions, ionic liquids, and other additives change the medium permittivity and conductivity.

Figure 6:
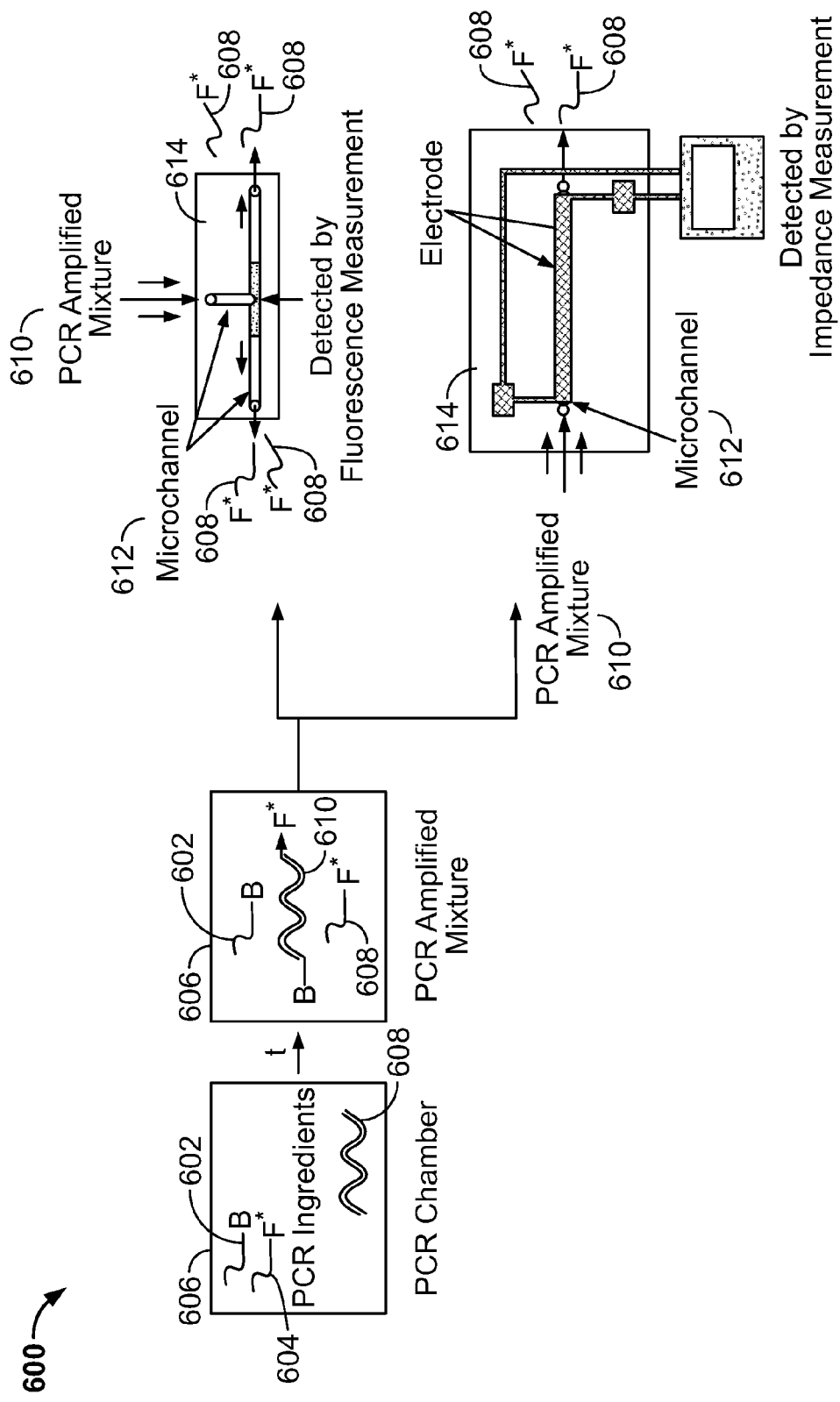
FIG. 6 is a schematic diagram of an example rapid target detection device showing two different example detection techniques.

FIG. 6 shows a block diagram of another example rapid target detection device 600 to detect bacteria, virus, and other harmful species in patients, the environment, or otherwise to, for example, monitor epidemics, terrorism, biowarfare, etc. that exceeds the capabilities of traditional DNA microarrays or real time PCR. The example rapid target detection device 600 involves a detection technique based on a modified PCR approach that utilizes the specific and strong binding property of streptavidin/avidin and biotin and tailored microfluidic fabrication techniques. Streptavidin is a tetrameric protein purified from the bacterium *Streptomyces avidinii*, and biotin ($C_{10}H_{16}N_2O_3S$), also known as vitamin H or $B_7$, is a water-soluble B-complex vitamin. Streptavidin has an extraordinarily strong affinity for biotin; the dissociation constant of the biotin-streptavidin complex is on the order of about $10^{-15}$ mol/L, ranking among one of the strongest known non-covalent interactions. Thus, the strong streptavidin-biotin bond can be used to attach various biomolecules to one another or onto a solid support (e.g., a nanostructure) to facilitate detection of various biomolecules, as described herein.

During the PCR protocol, two differently labeled primers, one biotinylated 602 and the other fluorescently labeled 604, are added to a PCR chamber 606 with the sample/target DNA 608 and are used to amplify the DNA of the target species of interest to enlarge the amount of single strand DNA (ssDNA) in the sample. Thus, amplified target DNA 610 is attached to a biotin group through one end of double string DNA (dsDNA) and the other end to fluorescently labeled dye.

The streptavidin/avidin may be functionalized on the device/chip channels or on the nano/microbeads, magnetic nanoparticle, carbon nanotube, nanowire, nanorod and/or other nanostructure (shown in other examples herein) contained in the chip. To accomplish the rapid detection of the PCR product, the amplified dsDNA is then exposed to streptavidin/avidin functionalized nanostructures by, for example, passing the amplified DNA 610 through trapped streptavidin/avidin functionalized nanostructure within a channel 612 in a microfluidic chip 614 to undergo a strong interaction between biotin and streptavidin or biotin and avidin. The passing of biotinylated amplified DNA 610 through trapped nanostructure within a channel 612 reduces the diffusion length and hence allows rapid interaction with the streptavidin attached to the surface of the nanostructure. Only the fluorescently labeled biotinylated dsDNA is specifically, rapidly, and strongly attached to the surface of the nanostructures.

Because of the strong bond, the interaction kinetics is extremely fast and the nanostructure platform reduces the transport time considerably. Moreover, the use of the nanostructures also offers higher surface area for interaction of biotin with streptavidin/avidin moiety and, thus, enhances detection sensitivity. The biotin-streptavidin/avidin binding is more specific than oligo-DNA double strand formation and allows for more robust and accurate assays with a large sample. In addition, the strong hybridization is particularly advantageous in large-throughput chips with a high flow rate, where hydrodynamic shear often tear off weakly hybridized DNAs. Further, because of the strong and specific binding, the hybridization step can immediately be followed by a rinsing buffer to remove all unattached fluorescent dye molecules 608.

Finally, detection may be accomplished by measuring the fluorescence intensity of the nanostructures. In addition, the use of functionalized carbon nanostructure, which has a high conductance, also facilitates the use of impedance measurement for rapid detection of the amplified product without an optical sensor, as described herein.

Figure 7:
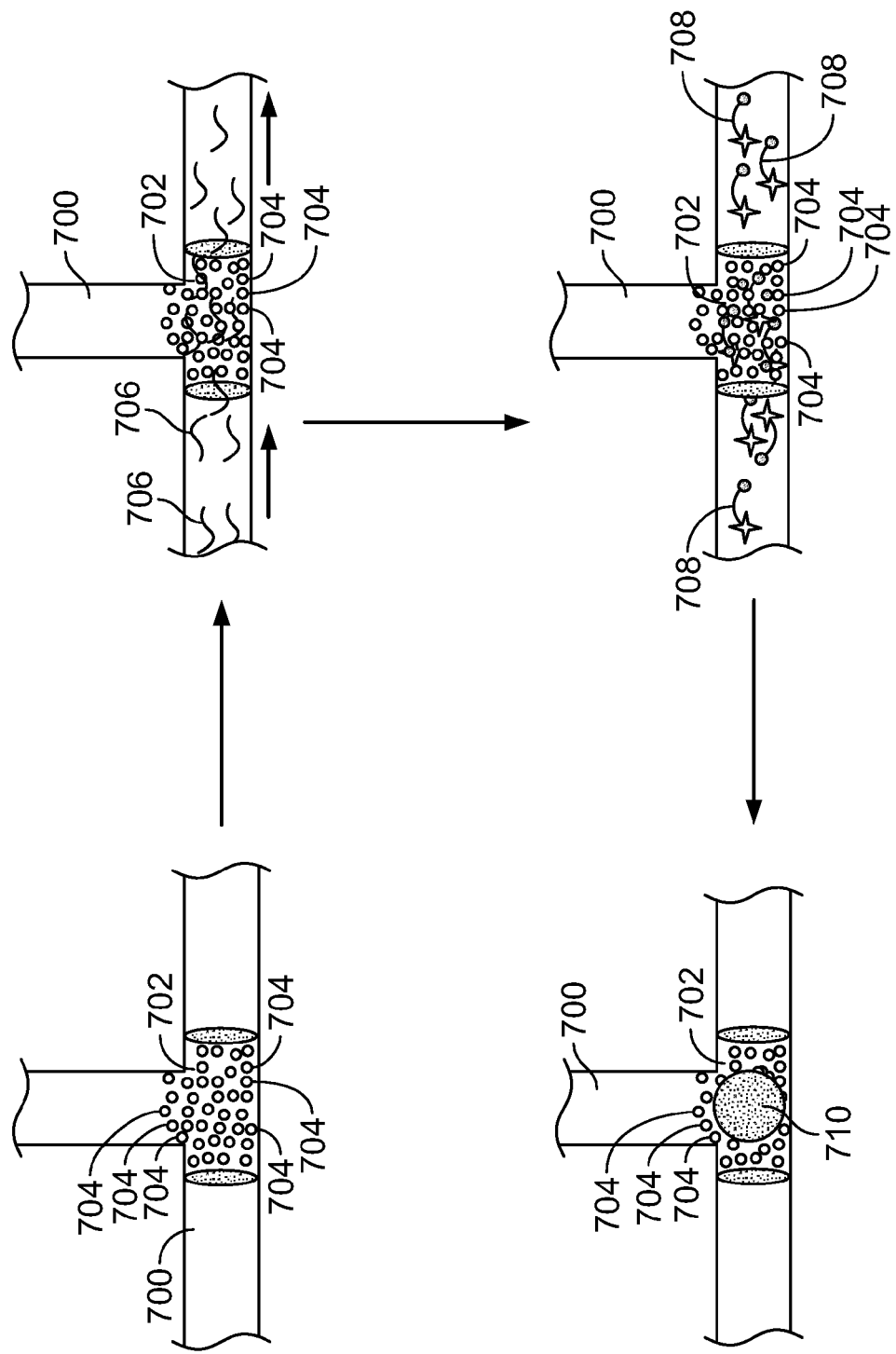
FIG. 7 shows a portion of example microfluidic channels on an example detection device.

FIGS. 7-11 show another example nanostructure based hybridization platform for genetic identification of a single target. FIG. 7 shows a portion of microfluidic channels 700 that form a chamber 702 containing nanostructure 704 which, in the illustrated example, are shown as probe functionalized silica beads but any suitable nanostructure may be used. The probe functionalized nanostructures (e.g., silica beads) are trapped and packed properly by passing a buffer solution that may be, for example, 4× standard saline citrate (SSC) hybridization buffer solution. After successful packing of the nanostructures 704, a volume of biotinylated ssDNA 706 such as, for example, 100 microliters, is passed through the packed chamber 702 at a temperature of, for example, about 50° C. at a flow rate of, for example, about 0.5 ml/h for hybridization with the complementary oligomers functionalized on the nanostructure (e.g., silica) surfaces. The passing of DNA 706 through packed chamber 702 reduces the separation distance between target DNA and oligomer probes on the surface of the nanostructures 704 and, thus, reduces hybridization time. Additionally, this nanostructure system offers a much greater surface area for hybridization, thus enhancing the detection sensitivity.

A wash solution or other liquid such as, for example, pure or deionized water, may be added to wash the unhybridized or non-specific DNA bound either to the surface of the nanostructure 704 or to the filter (as described below) from chamber 702. Further, hybridization detection may be accomplished through the addition of streptavidin bound fluorescent dye 708, thus taking advantage of the strong streptavidin-biotin binding reaction. Excess dye 708 is then washed from the channel, for example with a phosphate buffer saline (PBS) buffer solution, and a pattern and/or intensity of fluorescence 710 is measured and/or observed. Where the passing of DNA 706 through the channel 700 is considered the starting point for detection, then the detection time may be about two to three hours in this example, and the detection sensitivity is in the range of about 100 pM-nM, as described below.

The example nanostructure based detection technique described herein includes a plurality of components including, for example, (i) fabrication of the microchannel 700 on a glass slide 800 (FIG. 8), (ii) fabrication of filters within the microchannel 700 using a mixture of methacrylate photopolymers (FIG. 9), (iii) functionalization of oligomer probe on nanostructures, e.g., silica beads (FIG. 10), (iv) asymmetric PCR, and finally the successful execution of hybridization by passing the target DNA solution through the packed nanostructure microchannel within a device/chip (FIG. 7). As described above, hybridization of targets on nanostructures can be facilitated by the presence of an electric field such as, for example, a field produced by an AC current. The presence of the electric field greatly reduces the amount of time needed for hybridization. In some examples, hybridization may occur within one second as the detection targets are introduced to the nanostructures. Reduced hybridization time is beneficial for a high throughput portable device.

Figure 8:
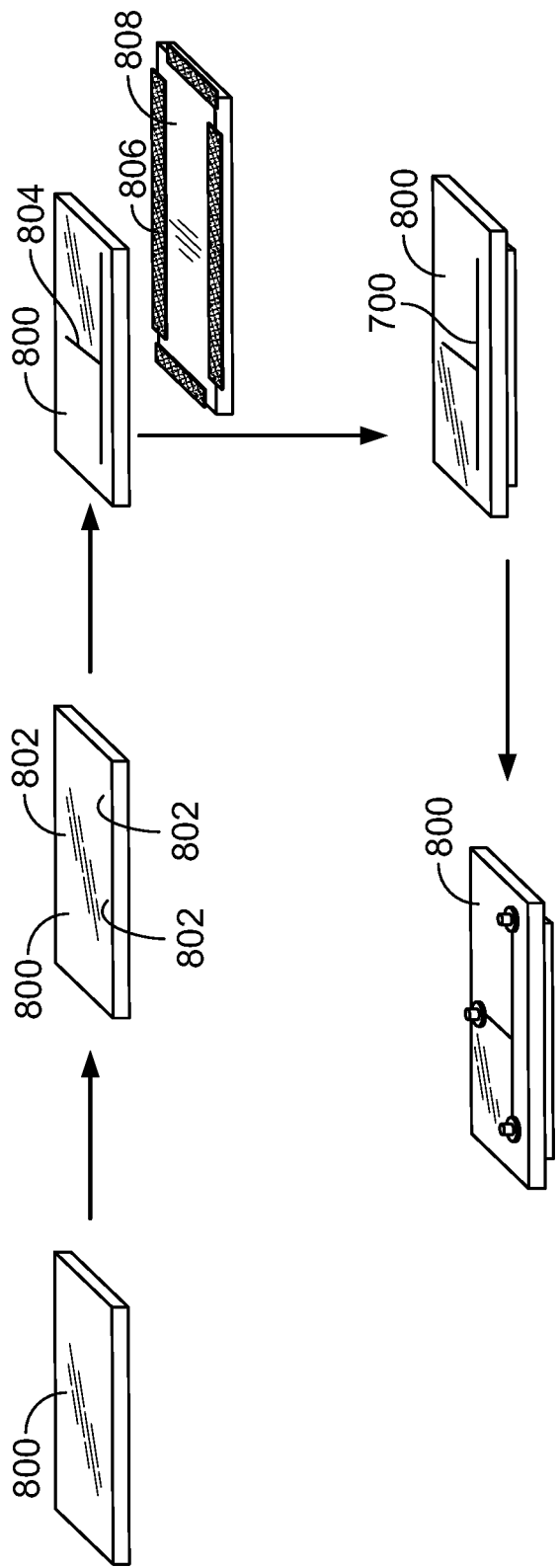
FIG. 8 shows an example fabrication of the example microchannels of FIG. 7 on an example glass slide.

FIG. 8 shows the fabrication of the microchannel 700 on the glass slide 800. Inlet and outlet ports 802 of the channel 700 are drilled. A mask layout 804 is combined with the glass slide 800, and a spacer tap 806 is coupled to a cover slip 808, to which a UV curable glue such as, for example, Loctite® 363 glue is added to couple the elements, which may be baked, for example, with UV energy for about five seconds. The channel 700 is then rinsed with solvents such as, for example acetone and methanol, and there may be a final UV bake for example, for two and a half minutes.

The fabrication of filter 900 (FIG. 9) is done inside the microchannel 700 by using a mixture of methacrylate photopolymers (monomer) along with a mixture of toluene and isobutanol (porogen). By changing the ratio of monomer and porogen, the pore diameter of the filter 900 can be manipulated. In some example, a filter with a pore size of about two microns is used with nanostructures sized at about ten microns. In addition, a mask is also combined and the combination is UV based for, for example, about one minute. After the bake, the mask is removed and the channel 700 is flushed with methanol for, for example, about two hours. The integrated UV bake, i.e., curing polymerization process, is used in both the microchannel 700 fabrication process and the microfilter 900 fabrication process to enable strong binding of the filter 900 with the microchannels 700.

In this example, nanostructure functionalization, PCR Design and hybridization detection may occur using any, all, or part of the examples described above. More specifically, in the example described herein, an amine conjugated 27-mer oligo probe is functionalized to the nanostructures (e.g., carboxylated silica beads) by coupling with water soluble carbodiimide (EDC) and N-hydroxysuccinimide (NHS). An example of this combination is illustrated in FIG. 10.

In some examples, to make the nanostructure based hybridization platform simpler and to avoid the denaturation of the target DNA, as the denatured ssDNA would recombine together before it reaches and interacts with probe functionalized nanostructures trapped within the microchannel, asymmetric PCR is performed to produce single stranded DNA. In this approach, an unequal concentration of primers is used (as opposed to, for example, normal, symmetric PCR). Initially, amplification starts exponentially, but as the lower concentrated primer is exhausted, the higher concentrated primer continues to amplify to produce single stranded DNA.

In this example, prior to adding the nanostructures 704 to the channel 702, a solution such as, for example, 2% Serum bovine albumin (BSA) solution may be passed through the microchannel 700 to prevent any non-specific binding of target DNA 706 and fluorescent dye 708 to the filters 900 and the surfaces of the channels 700.

Figure 11:
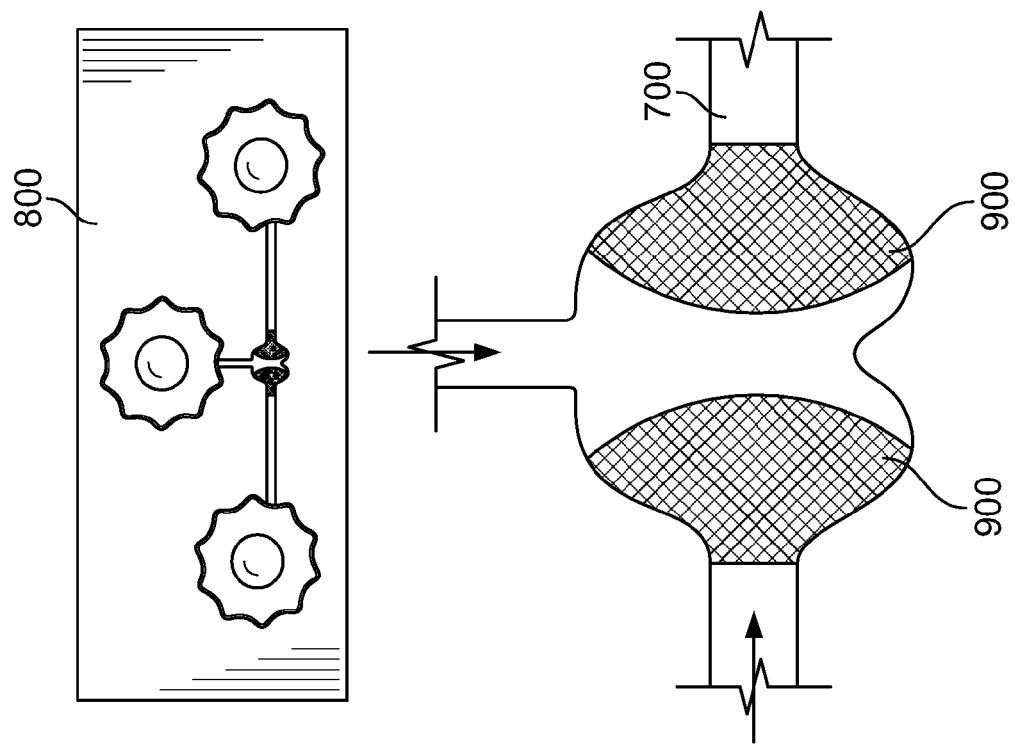
FIG. 11 shows a more detailed schematic diagram of the example detection device of FIG. 6 and a photographic image of the example device with an enlarged view of the example filter and example microchannel.
Figure 11:
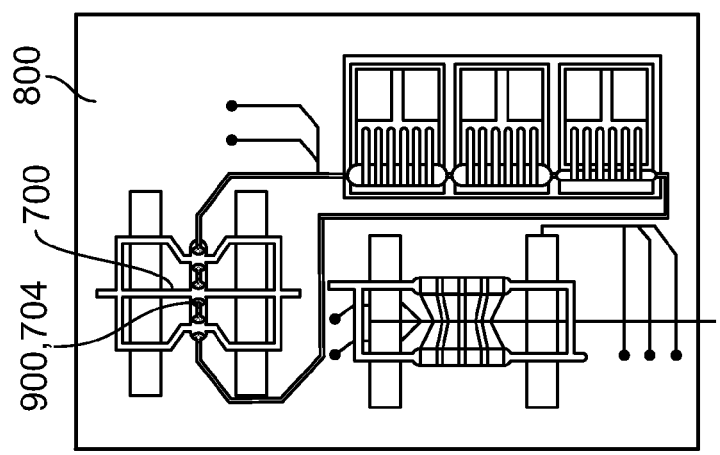
Figure 12:
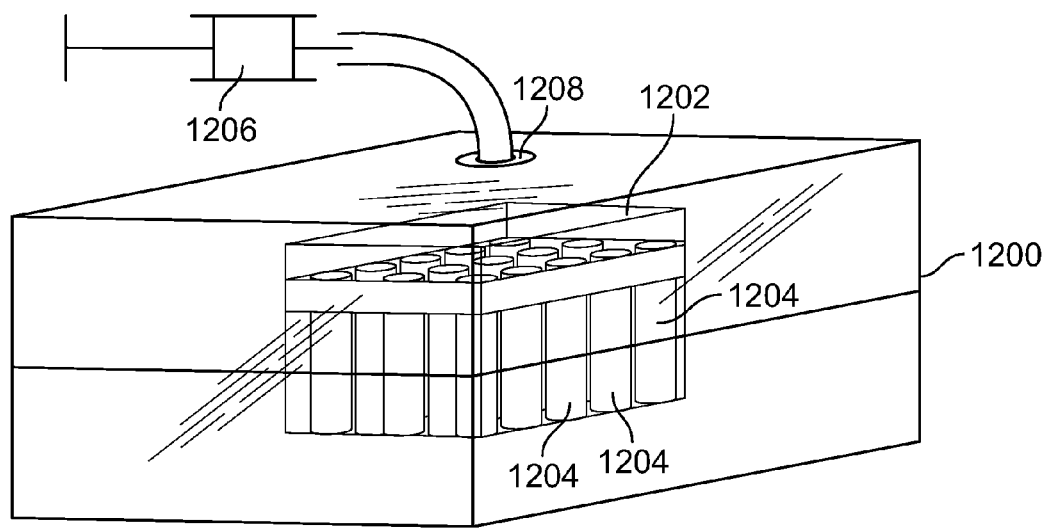
FIG. 12 is a schematic of an example multi-target detection unit using generic hybridization.

FIG. 11 is a more detailed schematic of the integrated and portable PCR detection chip 800. The filter 900 is shown in the channel 700 at the top of the chip 800. The example shown in FIGS. 7-11 can perform a single-target detection in, for example, thirty minutes, with most of the time used for the PCR cycles. As seen in FIG. 11, the fluorescent signal from the trapped nanostructures 706 can be easily picked up with a portable digital camera without a confocal facility. This disposable chip 800 contains on-chip pumping and valving, as well as diode sensor. Thus, the chip 800 is a self-contained portable genetic identification device/kit.

With respect to detection, due to the large surface area per unit volume of the oligo functionalized nanostructures, a micro-reservoir that is millimeters in dimension can capture all the target DNAs in a cubic centimeter volume sample with picomolar sensitivity. However, because all the fluorescent molecules are concentrated within a micro-liter volume, the fluorescent intensity is extremely high. As a reference, a single pixel on a DNA microarray (e.g., FIGS. 15-17) has an area of $10^{-2}$ cm$^2$ and that in a microliter of microbeads (50% by volume) is four orders of magnitude higher, with a proportionally larger fluorescent intensity. With this enhancement, laser excitation and confocal detection can be eliminated. A simple optical filter with a digital camera, a diode sensor or a CCD camera can be adequate for positive-negative identification, as shown herein. Rapid and portable positive-negative diagnostics have many important field-use applications as a preliminary screening step: epidemic control at ports/airports, avian flu monitoring of poultry imports, environmental monitoring, etc.

FIGS. 12-19 show other example implementations that may be used as multi-target DNA detection units with integrated PCR/detection units. The examples shown in FIGS. 12-19 may be extended to a continuous flow format with even higher throughput.

The examples shown detect and measure hybridization on nanostructures using either impedance detection or imaging. As described above, nanostructures include CNTs with a very sensitive impedance signal before and after hybridization. Both detection methods utilize the hybridization rapidity and sensitivity of the nanostructure technology and the changes in conductivity, size, induced dipole and dielectrophoretic mobility of the nanostructures due to hybridization, as described above.

In the example shown in FIGS. 12-19, the hybridization is generic, using streptavidin functionalized nanostructures and biotynated ssDNA that is PCRed separately with distinct primers, as described above. In this example, a replication or PCR module 1200 includes a removably couplable tube array box 1202 that includes a plurality of detection vials or tubes 1204, one of which is shown in greater detail in FIG. 13. A syringe or pump 1206 may be used to deliver the sample containing detection targets to the PCR module 1200 via an injection pore 1208. The sample is injected into the PCR module 1200 into a reservoir 1210. In addition, the PCR module 1200 includes a heating element (not shown) to provide a heat source to maintain a temperature such as, for example, about 50-90° C.

Figure 13:
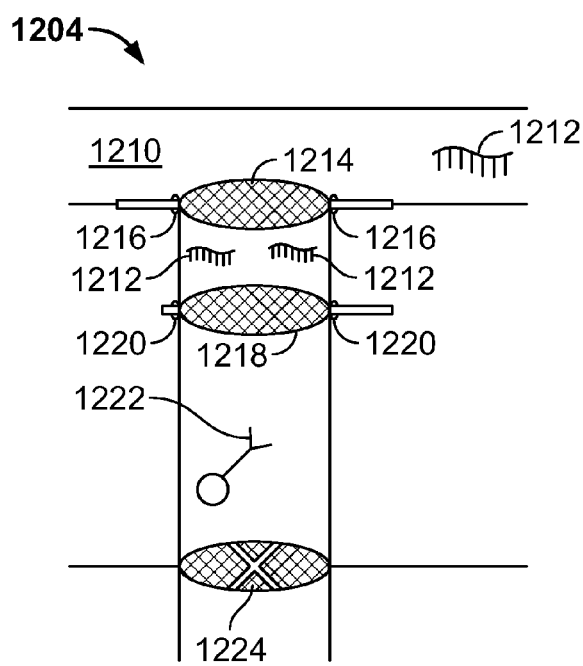
FIG. 13 is a schematic on an example detection subunit of the detection unit of FIG. 12.
Figure 14:
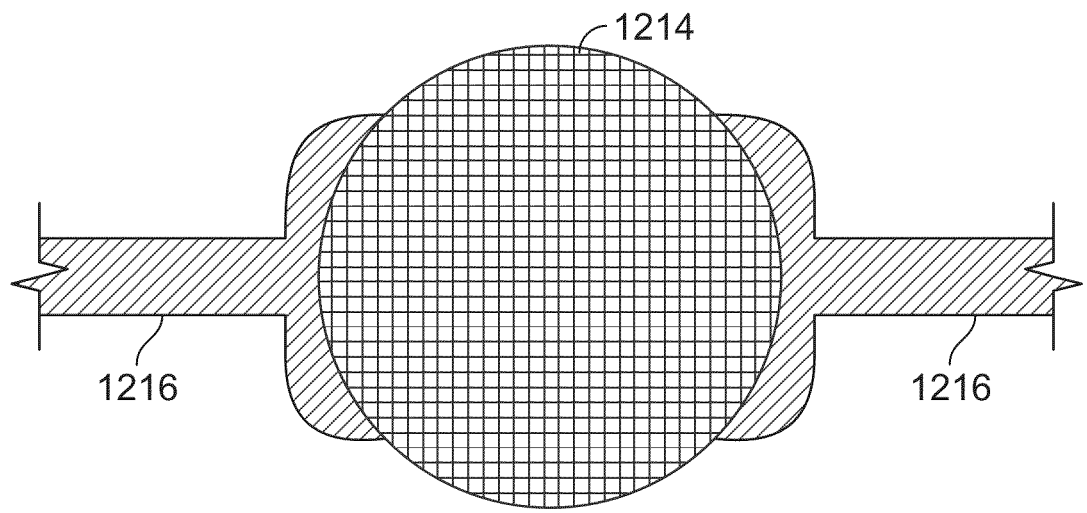
FIG. 14 is a schematic of an example membrane and example electrode pair of the example detection subunit of FIG. 13.

As shown in FIGS. 13 and 14, detection targets 1212 in the reservoir 1210 engage a first membrane 1214 that is coupled to at least a first electrode or a first pair of electrodes 1216. The first membrane 1214 is nanoporous or hydrogel and water permeable but does not permit the passage of other molecules, i.e., the detection targets are unable to pass through the membrane 1214. In particular, where the detection vials are too small to allow air bubbles to escape, the membrane 1214 should be water permeable. One example material for use for the membrane 1214 is Nafion. However, for tubes 1204 larger than 1 mm in radius, the membranes do not need to allow water passage. An electric field and/or voltage across the first electrodes 1216 dissolves, disintegrates or otherwise compromises the integrity of the first membrane 1214 to open at least one pore for molecular transit of the detection target 1212.

After the detection target 1212 passes the first membrane 1214, the detection target 1212 is PCRd with a particular primer/enzyme for the particular detection tube 1204. Because the amplicon of each PCR vial, i.e., detection tube 1204 is dominated by a specific target ssDNA, if it exists, and because each amplicon is delivered to separate detection units, there is no need to be specific at the identification stage.

The amplified detection targets engage a second membrane 1218 that is coupled to at least a second or a second set of electrodes 1220, which function similarly to the first membrane 1214 and first electrode(s) 1216.

After the application of a voltage across the second electrodes 1220, the second membrane is compromised and the detection targets 1212 pass from the PCR layer to a hybridization and detection layer. Here, the detection targets 1212 are hybridized using streptavidin functionalized nanostructures, as detailed above, to form a docked molecular probe or docked nanostructure 1222. This reaction occurs, for example, at about room temperature.

Figure 15:
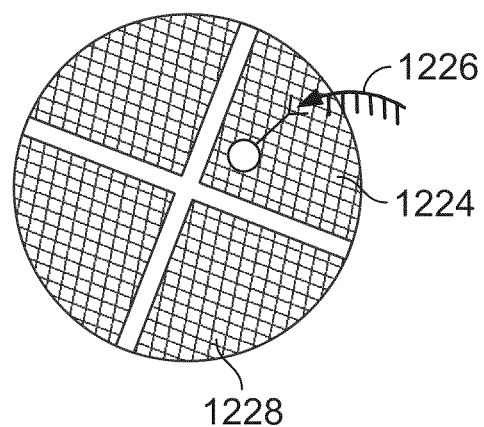
FIG. 15 is a schematic of an example impedance detector of the example detection subunit of FIG. 13.
Figure 16:
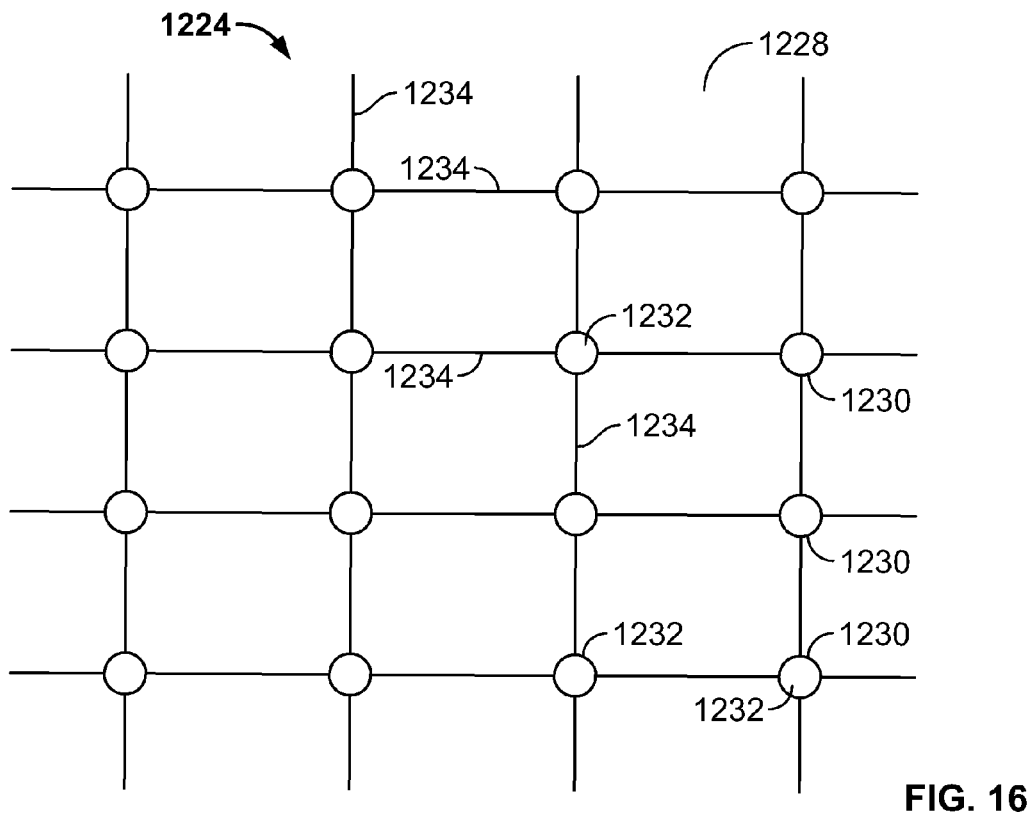
FIG. 16 is an enlarged view of an example electrode grid of the example impedance detector of FIG. 15.
Figure 17:
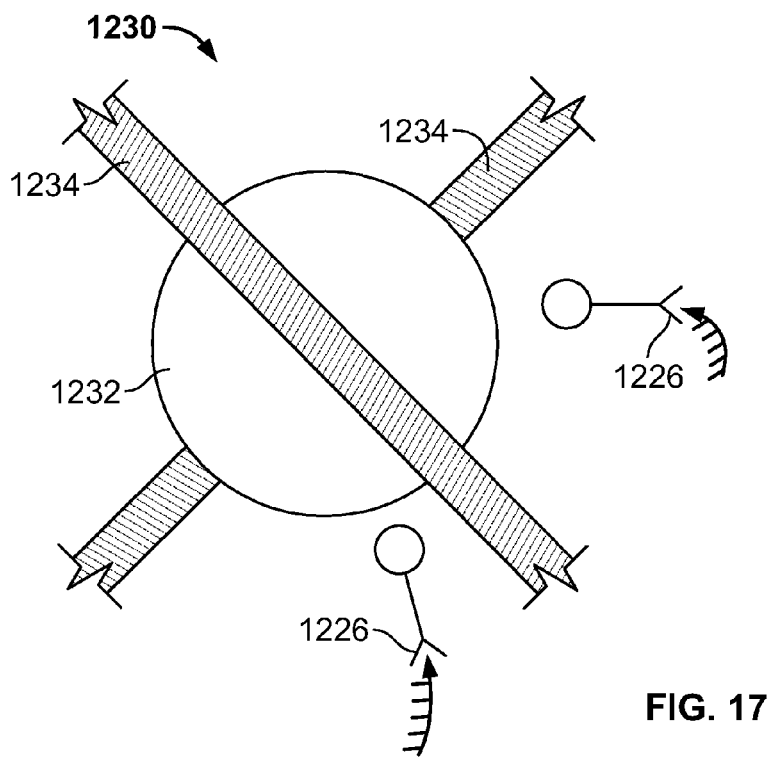
FIG. 17 is an enlarged view of an example array intersection of the example electrode grid of FIG. 16.

After hybridization, the docked molecular probe 1222 engages an impedance detector 1224 (FIGS. 13 and 15). The value of the impedance measured at the impedance detector 1224 provides an indication of the presence or absence of the detection targets 1212, as detailed herein. FIG. 16 is an enlarged view of a portion of an impedance detector 1224 shown in FIGS. 13 and 15. A micro electrode grid 1228 includes a plurality of pixels 1230, one of which is shown enlarged in FIG. 17. The pixels 1230 are addressable and, in some examples, are simultaneously addressable, while in other examples, the pixels 1230 are not addressable simultaneously. Each pixel 1230 includes a dielectric spacer 1232 at the intersection of two linear arrays 1234. The dielectric spacer 1232 allows a high field to be generated at the intersection of the two linear arrays 1234. The electric can manipulate movement of the docked nanostructures 1226 as described above. The docked nanostructures 1226 are moved to concentrate the docked nanostructures 1226 for imaging or impedance readout.

Figure 18:
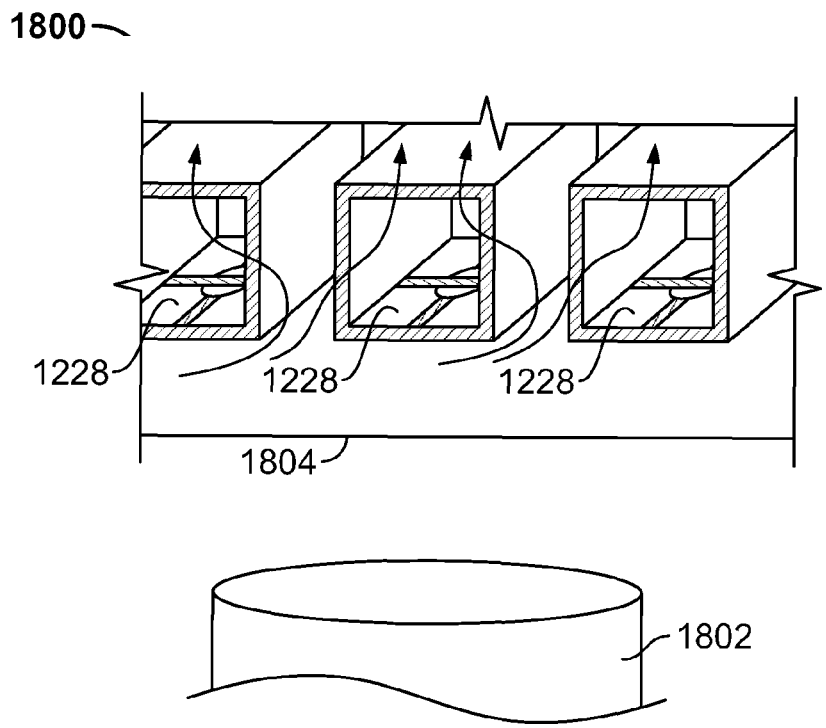
FIG. 18 is a schematic of an example imaging detector.
Figure 19:
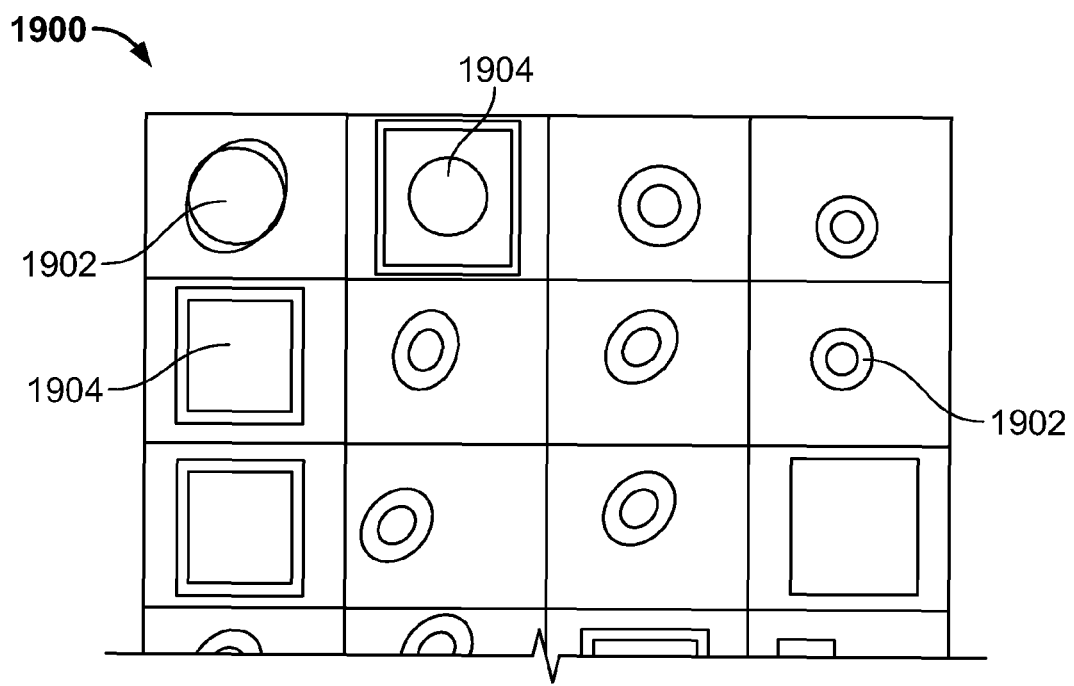
FIG. 19 is a schematic of an example image from the example imaging detector of FIG. 18.

FIG. 18 shows an example imaging detection unit 1800. In the example imaging detection unit 1800, a camera 1802 captures an image through an optically transparent cover lens or cover slip 1804 of one or more electrode grids 1228. The image of the grids 1228 will show whether a plurality of docked nanostructures 1226 have gathered. FIG. 19 shows an example image 1900. The example image 1900 shows congested areas 1902 where docked nanostructures 1226 have gathered and open areas where docked nanostructures 1226 have not gathered 1904.

Figure 20:
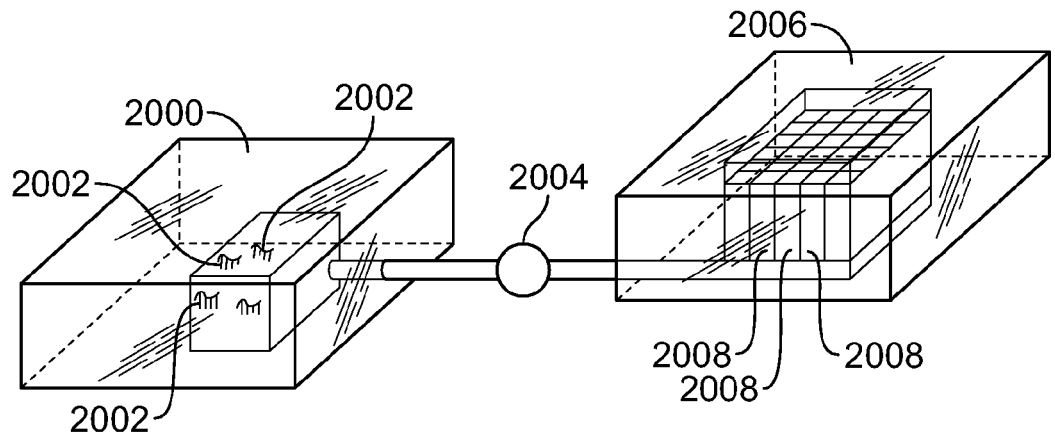
FIG. 20 is a schematic of an example multi-target detection unit using specific hybridization.
Figure 21:
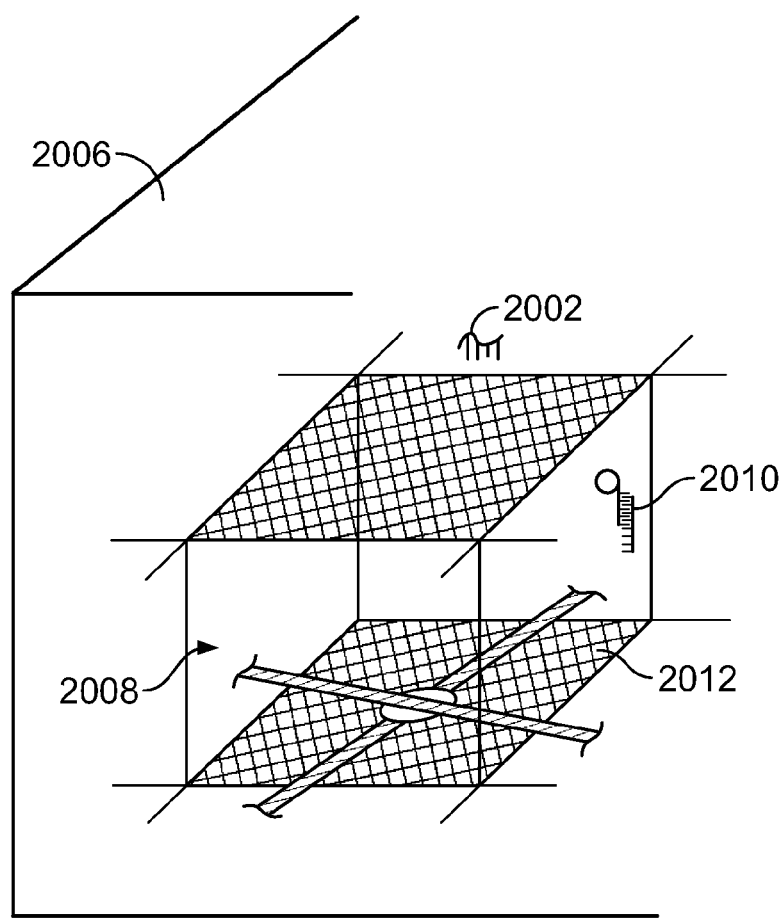
FIG. 21 is a schematic on an example detection subunit of the detection unit of FIG. 20.

Alternatively, in the example shown in FIGS. 20-21, the hybridization can be target-specific, between the target ssDNA and a complementary oligo functionalized on the nanostructures. In this alternative example, the PCR is performed in an alternative example replication or PCR unit 2000 that includes a reservoir with all the primers for all the possible target ssDNA to produce amplified detection targets 2002. Thus, the reservoir contains a collective of all types of amplicons for all types of targets included in the sample. A micropump/microvalve 2004 transfers the sample with the amplified detection targets 2002 to a hybridization/detection unit 2006 that contains a plurality of individual detection tubes or vials 2008, one of which is shown enlarged in FIG. 21. In some examples, the microvalve 1604 only needs to be opened once. The collective PCR amplicon is sent to all of the individual vials 2008, and each of the individual vials 2008 contains nanostructures functionalized with specific oligos. In some examples, the detection target 2002 is separated from the nanostructures in the hybridization layer under the opening of a membrane due to the presence of an electric field or voltage across electrodes, as detailed above. Once the detection target 2002 passes into the hybridization layer, hybridization occurs as detailed above. The hybridization occurs, in this example, at about 70° C.

After hybridization of the detection targets 2002 with the nanostructure to form a docket probe or docked nanostructure 2010, the docked nanostructure 2010 may engage an impedance detector 2012. The impedance detector 2012 detects the presence or absence of the detection target 2002 in a many similar to the impedance detector 1124, detailed above. In addition, the image detector 1800 may also be used in this example to detect the presence or absence of the detection targets 2002.

There are many advantages and benefits realized with the example, diagnostic devices/detection units described herein. For example, the examples described herein enable pathogen diagnostics to be more rapid, specific, sensitive and field-applicable. The advantages are numerous including, for example, early and rapid cancer detection or swift and pathogen-specific diagnosis of acute infections like sepsis, which would significantly increase patient survival rate. In addition to speed and specificity, the example devices and methods described herein have high portability allowing for field use, which may be particularly useful for field applications, such as epidemic control and for pathogen identification of multiple infectious pathogens that may threaten world health including, for example, avian influenza, SARS, hemolytic uremic syndrome and bloody diarrhea (*Escherichia coli* O157:H7), tuberculosis (*Mycobacterium tuberculosis*), anthrax (*Bacillus anthracis*), pneumonia (*Streptococcus pneumoniae*), malaria (*Plasmodium*), hepatitis (Hepatitis A, B, C, D, and E virus), and hemorrhagic fever (Ebola virus). The example devices and methods described herein may also be used for detecting *E. Coli* in food products and water sources, and identifying re-emerging pathogens with antibiotic resistance such as, for example, *pneumococci, enterococci, staphylococci, Plasmodium falciparum*, and *Mycobacterium tuberculosis* or malaria bacteria in third-world countries. For consumer oriented diagnostic devices/kits, the sample-contacting components of the example portable devices may be disposable. In addition, the example devices have high sensitivity, which is useful in detecting pathogens involving a smaller number of targets such as, for example, a situation experienced with bioterrorism and environmental applications.

The examples described herein are lab-on-a-chip microfluidic platforms that allow a large-throughput continuous-flow format by moving discrete samples or continuous streams from one station to the next within a single chip, and without human intervention. In addition, device specificity is enhanced because the desired targets (e.g., specific DNA segments) are concentrated near the probes by the microfluidic means and DEP as described herein.

Additionally, the AC electrokinetic platforms described above are extremely portable as they can be driven by hand-held power supplies like those within a cell phone. A high-frequency (e.g., greater than about 100 kHz) AC field typically has a period shorter than the Faradaic reaction time of the respective voltage, and, consequently, bubbles and net generation of ionic products do not occur at the electrodes. As such, electrodes can be embedded within the example devices to allow for more precise fluid management.

Furthermore, one of the major advantages of the examples described herein is the ability to use the example devices for multi-target diagnostics. Even if only one target (e.g., one pathogen) is to be detected, multiple DNA targets from its genome are often required to make an accurate identification.

In addition, functionalizing molecular probes onto the surface of submicron nanostructures that have small dimensions, large numbers, and large surface area-to-volume ratios increases detection sensitivity. For example, a 100 microliter sample of a 1% nanostructure (e.g., micron-sized colloid) suspension contains a billion nanostructures with a total surface area of 1 $cm^2$. Compared to a pixel area of 1 $mm^2$ for traditional DNA microarrays, these nanostructures offer a capturing area that is eight-orders of magnitude larger and a comparable increase in sensitivity. Furthermore, in the same sample, the average separation between nanostructures is three-orders of magnitude smaller than the linear dimension of the sample. For the case of a small number of detection target molecules present, this translates into a maximum of six-orders of magnitude reduction in diffusion time, which is much higher than any convection-enhanced mass-transfer rate.

There are other potential benefits for this nanostructure platform. If these nanostructures can be assembled and dispersed within the microchannels, the nanostructures can form micro-CSTRs, microchromatographs, and microplugflow reactors, and, hence, invoke advantages of these reactor designs: a yield better than the thermodynamic yield for an open-flow CSTR, separation to enhance selectivity of parallel docking reactions, and low dispersion to enhance the yield of irreversible reactions.

In addition, in those examples in which a PCR technique is combined with the strong streptavidin/avidin and biotin interaction, the genetic identification of detection target species is simpler, more rapid, robust and sensitive. The examples described herein significantly reduce response time while increasing sensitivity. Thus, the portable PCR chips or other devices described herein provide on-field applications. The examples described herein also eliminate the need for a multi-step stir, wash and rinse protocol for fluorescent detection that requires lab-trained technicians and laboratory facilities. In addition, the examples and methods described herein remove the need for a lab-bound confocal facility to facilitate detection and hour-long hybridization time. Also, light emitting diodes (LEDs) coupled with optical filters and silicon photodiodes may be used to further develop and miniaturized an optical detection platform.

Furthermore, the geometry of the example microchannels and nanostructures described herein relaxes sensitivity and portability limits experienced with conventional microfluidic designs. The large surface area to volume ratio within a microchannel allows more surface probes to be functionalized to the walls of the channel, which significantly increases the probability of capturing targets present in minute concentrations, and, thus, improves the sensitivity of the respective diagnostic assay.

The ability of the example device to detect infectious pathogens enables mounting a quick and effective response to outbreaks of pathogen-caused disease. An operator such as, for example, a clinical microbiologist, nurse, or other technician can determine if there are pathogens present in a sample (be it a clinical sample, food sample, environmental sample, etc.), and if so, identify the type and quantity of the pathogens. There may be just a few (e.g., less than about five) identified pathogens to hundreds, and the number of each type may vary over several orders of magnitude such as, for example, from a few to millions of colony forming units (CFU) per milliliter of sample.

Although certain example methods, apparatus and articles of manufacture have been described herein, the scope of coverage of this patent is not limited thereto. On the contrary, this patent covers all methods, apparatus and articles of manufacture fairly falling within the scope of the appended claims either literally or under the doctrine of equivalents. Furthermore, any of the examples devices and/or methods described herein may be combined in whole or in part.

What is claimed is:

1. A method of detecting a plurality of target nucleic acids, the method comprising:
    continuously flowing a sample solution comprising the target nucleic acids through a microfluidic device having at least a first surface with a first electrode and a second surface displaced from the first surface at a distance and having a second electrode opposing the first electrode;
    provided a first and second functionalized nanostructure in solution to the microfluidic device, wherein the first nanostructure is formed by functionalizing a first probe complementary to a first target nucleic acid and the second nanostructure is formed by functionalizing a second probe complementary to a second target nucleic acid;
    applying an electric current to the electrodes;
    using the electric field created by the electric current applied to the electrodes to move the nanostructures;
    trapping the nanostructures within the electric field;
    mixing the sample solution and the solution providing the nanostructure;
    hybridizing the target nucleic acids with the nanostructures in the presence of the electric field;
    hydrodynamically shearing at least one of a non-target or a weakly hybridized target nucleic acid from the nanostructures, wherein the application of the electric current to the nanostructures causes the nanostructure hybridized with the first target to move in a first direction and causes the nanostructure hybridized with the second target to move in a second direction, and wherein the first target and the second target are sorted based on the first direction or the second direction; and
    evaluating the trapped nanostructures by measuring an electrical impedance between the electrodes to determine a presence, an absence, or a quantity of the first or second target nucleic acids.

2. A method as defined in claim 1, wherein the electric current induces dielectrophoresis.

3. A method as defined in claim 1, wherein a presence of an increased pressure does not impede the method.

4. A method as defined in claim 1, wherein a copy of at least one of the plurality of target nucleic acids is produced via a polymerase chain reaction.

5. A method as defined in claim 1, wherein the electric field has at least a first frequency and a second frequency, and wherein the nanostructures move in a first direction at the first frequency and in a second direction at the second frequency.

6. A method as defined in claim 1, wherein the plurality of nanostructures form a pattern dependent on a frequency of the electric field.

7. A method as defined in claim 1, wherein the electric current creates a non-uniform electric field across the microfluidic device.

8. A method as defined in claim 1, wherein the nanostructures are one or more of carbon nanotubes, nanobeads, nanowires, nanocolloides, nanoparticles, nanorods, quantum dots, nanocrystals, liposomes, silica beads, latex beads, gold colloids or other structures with dimensions less than one micron.

9. A method as defined in claim 1, wherein the one or more of the first or second probes includes one or more of a oligomer, a fluorophore, a carboxyl group, or a streptavidin.

10. A method as defined in claim 1 further comprising pretreating the sample.

11. A method as defined in claim 10, wherein pretreating includes at least one of filtering or removal of inhibitors.

12. A method of detecting a target nucleic acid, the method comprising:
    obtaining a sample including the target nucleic acid;
    functionalizing a first molecular probe complementary to a first target nucleic acid to a first nanostructure and functionalizing a second molecular probe complementary to a second target nucleic acid to a second nanostructure;
    coupling the functionalized nanostructures to a chamber having a first surface with a first electrode and a second surface displaced from the first surface at a distance and having a second electrode opposing the first electrode;
    flowing the target nucleic acids through the chamber to hybridize the first target nucleic acid to the first functionalized nanostructure and to hybridize the second target nucleic acid to the second functionalized nanostructure;
    causing the nanostructure hybridized with the first target to move in a first direction and causing the nanostructure hybridized with the second target to move in a second direction, wherein the first target and the second target are sorted based on the first direction or the second direction; and detecting at least one of a presence, an absence, or a quantity of the first or second target nucleic acids by measuring an electrical impedance between the electrodes.

13. A method as defined in claim 12, wherein at least one of the first or second target nucleic acids is replicated through a polymerase chain reaction and flowing the amplified mixture through the chamber.

14. A method as defined in claim 13, wherein the polymerase chain reaction uses two differently labeled primers.

15. A method as defined in claim 14, wherein one of the primers is biotinylated and the other is fluorescently labeled.

16. A method as defined in claim 12 further comprising applying an alternating current electric field to the chamber wherein the presence of the electric field improves hybridization rate and yield.

17. A method of detecting target nucleic acids comprising:
    placing a solution having a plurality of functionalized nanostructures within a channel having a first surface with a first electrode and a second surface displaced from the first surface at a distance and having a second electrode opposing the first electrode, wherein a first one of the plurality of functionalized nanostructures includes a oligonucleotide probe complementary to a first target nucleic acid and wherein a second one of the plurality of functionalized nanostructures includes a oligonucleotide probe complementary to a second target nucleic acid;
    applying an alternating current field to the first and second electrodes to focus and trap the nanostructures;
    flowing a sample including the target nucleic acids within the channel and through the trapped functionalized nanostructures;
    hybridizing the target nucleic acids with at least one of the nanostructures;
    hydrodynamically shearing at least one of a non-target or a weakly hybridized target nucleic acid from the nanostructures, wherein the application of the electric current to the nanostructures causes the nanostructure hybridized with the first target to move in a first direction and causes the nanostructure hybridized with the second target to move in a second direction, and wherein the first target and the second target are sorted based on the first direction or the second direction; and evaluating the trapped nanostructures by measuring an impedance signal during the sample flow to determine a presence, an absence, or a quantity of the target nucleic acids.

18. A method as defined in claim 17, wherein the applied electric field is an alternating current field with a period shorter than the Faradaic reaction time corresponding to the respective voltage.

19. A method as defined in claim 18, wherein the alternating current applied to the first and second electrodes creating the electric field is also used to provide the measurement of electrical impedance between the electrodes.

20. A method as defined in claim 17, wherein the nanostructures are carbon nanotubes.

21. A method as defined in claim 20, wherein the carbon nanotubes trapped at the electrodes focus the electric field thereby concentrating targets between the first and second electrodes.

22. A method as defined in claim 21, wherein the carbon nanotubes enhance dielectropheretic forces within the channel.

23. A method as defined in claim 17, wherein hybridization yield and rate are enhanced in the presences of an electric field.

24. A method as defined in claim 17, wherein the nanostructures are trapped by force induced by dielectrophoresis.

25. A method as defined in claim 17, wherein the nanostructures are evaluated based on a change in impedance signal before and after hybridization with the target nucleic acids with the shift in impedance relevant to the number of hybridized targets.

* * * * *